United States Patent
Lu et al.

(10) Patent No.: US 8,728,346 B2
(45) Date of Patent: May 20, 2014

(54) PREPARATIONS OF SUSPENSIONS

(75) Inventors: Gaoqing Lu, Mt. Ommaney (AU); Zhiping Xu, Riverhills (AU)

(73) Assignee: The University of Queensland, St. Lucia (AU)

( * ) Notice: Subject to any disclaimer, the term of this patent is extended or adjusted under 35 U.S.C. 154(b) by 163 days.

(21) Appl. No.: 12/787,780

(22) Filed: May 26, 2010

(65) Prior Publication Data
US 2010/0233286 A1    Sep. 16, 2010

Related U.S. Application Data

(63) Continuation of application No. 11/722,650, filed as application No. PCT/AU2005/001948 on Dec. 21, 2005, now abandoned.

(30) Foreign Application Priority Data

Dec. 24, 2004  (AU) ................................. 2004907326

(51) Int. Cl.
| C09K 3/00 | (2006.01) |
| C01B 31/00 | (2006.01) |
| C01G 1/04 | (2006.01) |
| C01C 1/26 | (2006.01) |

(52) U.S. Cl.
USPC ...... 252/182.33; 423/414; 423/416; 423/417; 423/420

(58) Field of Classification Search
USPC .............. 252/182.33; 423/420, 414, 416, 417
See application file for complete search history.

(56) References Cited

U.S. PATENT DOCUMENTS 3,539,306 A * 11/1970 Kumura et al. ............... 423/432
6,287,532 B1 * 9/2001 Okada et al. ............... 423/420.2

FOREIGN PATENT DOCUMENTS

| CN | 1415578 A * | 5/2003 | ............... C01F 7/00 |
| EP | 0989095 A1 | 3/2000 | |
| JP | H10-001311 | 1/1998 | |
| JP | H11-255973 | 9/1999 | |
| JP | 2000-119510 | 4/2000 | |
| JP | 2000-144095 | 5/2000 | |
| WO | WO 03/037787 A1 | 5/2003 | |

OTHER PUBLICATIONS

Cavani et al. Catalysis Today, vol. 11 1991 pp. 173-301.*
Liu et al. 2003 "Liquid-Crystalline Phases of Colloidal Dispersions of Layered Double Hydroxides" *Chemistry of Materials* 15(17):3240-3241.

* cited by examiner

*Primary Examiner* — Patrick Ryan
*Assistant Examiner* — Aaron Greso
(74) *Attorney, Agent, or Firm* — Knobbe, Martens, Olson & Bear, LLP

(57) ABSTRACT

A method for preparing a suspension of LDH particles comprises the steps of preparing LDH precipitates by coprecipitation to form a mixture of LDH precipitates and solution; separating the LDH precipitates from the solution; washing the LDH precipitates to remove residual ions; mixing the LDH precipitates with water; and subjecting the mixture of LDH particles and water from step (d) to a hydrothermal treatment step by heating to a temperature of from greater than 80° C. to 150° C. for a period of about 1 hour to about 144 hours to form a well dispersed suspension of LDH particles in water.

24 Claims, 5 Drawing Sheets

Individual: 30-50 nm
Aggregate: 1-10 μm

Individual: 30-50 nm
Aggregate: 1-10 μm

In ethanol         In water

MgAl-NO3-LDH

PREPARATIONS OF SUSPENSIONS

CROSS-REFERENCE TO RELATED APPLICATIONS

This application is a continuation of application Ser. No. 11/722,650, filed May 5, 2008, which is United States National Phase under 35 U.S.C. §371 of International Application PCT/AU2005/001948, filed Dec. 21, 2005 designating the U.S., and published in English as WO 2006/066341 A1 on Jun. 29, 2006, which claims priority to Australian Patent Application No. 2004907326, filed Dec. 24, 2004.

BACKGROUND OF THE INVENTION

1. Field of the Invention

The present invention relates to a method for preparing a suspension. The present invention also extends to a suspension. In some embodiments, the present invention relates to a stable suspension containing layered double hydroxide particles and to a method for preparing such suspensions.

2. Description of the Related Art

Layered double hydroxides (hereinafter referred to as "LDHs") are mixed hydroxides of divalent and tri-valent metals having an excess of positive charge that is balanced by interlayer anions. They can be represented by the general formula (1):

$$M^{II}_{1-x}M^{III}_x(OH)_2A^{n-}_{x/n} \cdot yH_2O \qquad (1)$$

where $M^{II}$ and $M^{III}$ are di- and tri-valent metal ions respectively and $A^{n-}$ is the interlayer anion of valance n. The x value represents the proportion of trivalent metal to the total amount of metal ion present and y denotes variable amounts of interlayer water.

Common forms of LDH comprise $Mg^{2+}$ and $Al^{3+}$ (known as hydrotalcites) and $Mg^{2+}$ and $Fe^{3+}$ (known as pyroaurites), but LDHs containing other cations including Ni, Zn, Mn, Ca, Cr, and La are known. The amount of surface positive charge generated is dependent upon the mole ratio of the metal ions in the lattice structure, and the conditions of preparation as they affect crystal formation.

LDH compounds are of interest because they are considered to be useful as catalysts, catalyst precursors, catalyst supports, absorbents, anion exchangers, PVC stabilisers, flame retardants, medicinal antacids and as material for use in nanocomposites.

LDH particles are typically plate like in morphology. During preparation of LDH compounds, the plate like particles tend to aggregate together to form larger particles, typically having particle sizes in the range of microns or above. It has been found to be difficult to disperse the aggregated particles because of the strong interactions between the platy LDH nanosheets, such as electrostatic attraction via the common surface anions and hydrogen-bonds via water molecules.

LDHs can be prepared by forming a mixed solution containing the $M^{2+}$ and $M^{3+}$ ions in solution and adjusting the pH of the solution to an alkaline pH. This results in the coprecipitation of the LDH as solid particles. Other synthetic pathways to form LDHs, particularly those containing magnesium, include synthesis from $Mg(OH)_2$ (brucite) and MgO (calcined magnesia) via incorporating trivalent metal ions, such as $Al^{3+}$, and including anions. A number of other methods for producing LDHs have also been described.

Liu et al, "Liquid—Crystalline Phases of Colloidal Dispersions of Layered Double Hydroxides", Chem. Mater. 2003, 15, 3240-3241, described the synthesis of colloidal Mg/Al LDH that was carried out using a non-steady coprecipitation method. The pH of an aqueous solution of mixed magnesium and aluminium chlorides was raised to 9.5 by adding 3.5 M $NH_3 \cdot H_2O$ under vigorous stirring. The resulting precipitate was aged at room temperature for one hour. After filtration, the filter cake was washed thoroughly with deionised water. It was then collected and closed in a glass bottle for peptization in a thermostat at 80° C. for 24 hours. Well dispersed colloidal LDH particles were obtained. Transmission electron microscopy showed that most particles were roughly monodispersed platelets, hexagonal in shape, with diameters between 50 and 80 nm, and the electron diffraction pattern showed Mg/Al LDH particles were well-crystallined with hexagonal symmetry. The particle thickness of about 5 nm was also revealed. The Zeta potential of the particles was measured to be +39 millivolts. Dispersions of the LDHs in water were shown to form liquid crystalline phases.

J.-M. Oh et al, "The Effect of Synthetic Conditions on Tailoring the Size of Hydrotalcite Particles", Solid State Ionics, 151 (2002), 285-291, investigated preparation of hydrotalcites. In particular, clear metal solutions containing magnesium and aluminium were titrated up to pH of approximately 11 with sodium hydroxide solution containing sodium carbonate and aged in an autoclave at 100° C. for 12, 24, 48, 72 hours, and also at 100° C., 125° C., 150° C., 180° C., for 48 hours respectively. The particle sizes were analysed and it was found that increasing aging time and increasing temperature result in increasing particle size. The average particle size ranged from 85 nm (for aging at 100° C. for 12 hours) to 340 nm (for aging at 180° C. for 48 hours).

European patent application no. 987328 in the name of Jin Ho Choy described a bio-inorganic hybrid composite for retaining and carrying bio-materials with stability and reversible dissociativity. The bio-inorganic hybrid composite was prepared by forming a stable layered double hydroxide in which anions are intercalated and subjecting the intercalated anions to an ion exchange reaction with a bio material. The bio material is suitably nucleoside-5'-monophosphate, nucleoside-5'-triphosphate, or a gene material with a size of 500-1000 base pairs.

The applicant does not concede that the prior art discussed above forms part of the common general knowledge in Australia or elsewhere.

Throughout this specification, the word "comprising" or its grammatical equivalents shall be taken to have an inclusive meaning unless the context clearly indicates otherwise.

SUMMARY OF THE INVENTION

In a first aspect, the present invention provides a method for preparing a suspension of LDH particles comprising the steps of:
a) preparing LDH precipitates by coprecipitation to form a mixture of LDH precipitates and solution;
b) separating the LDH precipitates from the solution;
c) washing the LDH precipitates to remove residual ions;
d) mixing the LDH precipitates with water; and
e) subjecting the mixture of LDH precipitates and water from step (d) to a hydrothermal treatment step by heating to a temperature of greater than 80° C. to 150° C. for a period of about 1 hour to about 144 hours to form a suspension of LDH particles in water.

Suitably, the hydrothermal treating step is carried out whilst suppressing boiling.

The LDH may have a composition as given in formula (1) above. This formula may also be written as formula (2):

$$M^{II}_n M^{III}(OH)_{2(n+1)} X \cdot yH_2O \qquad (2)$$

wherein X= one or more anions or negatively charged material to balance charge in the hydroxide layer. X is typically present in the interlayer space in the LDH material.

$M^{II}$ is suitably Mg, although other metal ions of valence 2+ may also be used. $M^{III}$ is suitably Al. It will be appreciated that other metal ions of valence 3+ may also be used. Examples of other metal ions that maybe used include:

$M^{II}$: Fe, Co, Ni, Cu, Zn5 Mn, Pd, Ti, Cd and Ca
$M^{III}$: Co, Fe, Mn, Ga, Rh, Ru, Cr, V, Ia, Y, Gd and La.

These lists should not be considered to be limiting.

The coprecipitation step suitably involves the steps of forming a mixed metal ion solution containing the appropriate metal ions and adding that solution into an alkaline material to form LDH precipitates. Suitably, the alkaline material is an alkaline solution. Precipitation of layered double hydroxides typically occurs when the pH of the mixed metal ion solution is raised to greater than 6-7 depending on the metal ions used. The alkaline solution that is used in the present invention is suitably a sodium hydroxide solution, together with either sodium bicarbonate or sodium carbonate if necessary. However, it will be appreciated that numerous other alkaline solutions, such as ammonia solutions, KOH, $NaHCO_3$, $KHCO_3$, $Na_2CO_3$, $K_2CO_3$, and possibly some organic amines, such as methylamine, ethylamine may also be used in the process of the present invention. This list should not be considered to be exhaustive and other alkaline solutions may also be used in the present invention.

As will be well known to the person skilled in the art, the solutions are suitably stirred or agitated during the mixing and precipitation steps. The mixed metal ion solution may suitably be prepared by dissolving appropriate salts of the metals in water. The metal salts are, for example, chlorides, nitrates, sulfates or any other metal salts that are readily soluble and inexpensive. Alternatively, the appropriate metals may be placed in acid solutions to be thereby dissolved to form the mixed metal ion solution. Acids that may be used include hydrochloric acid (HCl), nitric acid ($HNO_3$), sulfuric acid ($H_2SO_4$) as well as many other organic carboxylic acids, such as methanoic acid, acetic acid.

The coprecipitation step suitably involves adding the mixed metal ion solution to an alkaline solution with appropriate stirring or agitation. It is preferred that the mixed metal ion solution and the alkaline solution are rapidly mixed together. Suitably, the mixed metal ion solution and the alkaline solution are mixed together within a time period of less than 1 minute, more suitably within a time period of less than 20 seconds, even more suitably in a time period of less than 5 seconds, most suitably in a time period of less than 2 seconds.

Precipitation of the LDH is rapid once the pH has risen to the required level. Therefore, rapid mixing of the mixed metal ion solution and the alkaline solution results in precipitation of the LDH precipitates over a short period of time.

The precipitation step may take place at room temperature, although other temperatures may be used during the coprecipitation step. Indeed, temperatures of up to 50° C. during the precipitation step have been shown to have little effect on the particle size distribution obtained by the present invention.

Once the LDH precipitates have precipitated, a mixture of the LDH precipitates and solution is obtained. This mixture has a pH that depends upon the ions used and the relative amount of alkaline material added. For MgAl-LDH, the pH is generally 7.5-8.0. The particles and the solution are suitably left in contact with each other for a period of no more than 30 minutes following precipitation of the LDH precipitates. More suitably, the LDH precipitates and the solution are left in contact with each other for a period not exceeding 20 minutes, even more suitably not exceeding 10 minutes, yet more suitably not exceeding 5 minutes and most suitably left in contact for a period not exceeding 1 minute. During such contact, vigorous stirring is generally applied.

The LDH precipitates and the solution are then separated from each other. Any suitable method of separating solid particles from a liquid solution may be used. Examples include centrifugation and filtration.

Following separation, the LDH precipitates are washed. The washing step removes any residual ions in the mixed solution. It also removes any residual alkaline material. The LDH precipitates may be washed one or, more preferably, two or more times to ensure that substantially all residual ions are removed from the LDH precipitates. De-ionized water is suitably used to wash the LDH precipitates.

The LDH precipitates are then mixed with water. Suitably, the precipitates are dispersed in water, especially de-ionized water. This mixture is then subjected to the hydrothermal treating step (step (e)). The hydrothermal treating step is conducted by heating the mixture of LDH precipitates and water to an elevated temperature whilst, in most cases, suppressing boiling. The temperature in the hydrothermal treating step is from greater than 80° C. to 150° C. Suitably, the temperature used in the hydrothermal treating process is between 80° C. and 120° C., more suitably between 90 and 110° C. and most suitably at about 100° C. The mixture of water and LDH particles is suitably held at the elevated temperature for a period of from 1 to 144 hours, more suitably from 2-72 hours, more suitably 4-48 hours, even more suitably 4-24 hours. A well dispersed suspension of LDH particles in water is obtained following the hydrothermal treatment step.

Suppression or prevention of boiling, if required, is typically achieved by maintaining the pressure in the hydrothermal treating steps sufficiently high to stop boiling. Suitably, the pressure in the hydrothermal treating step is the autogenous pressure of the mixture at the elevated temperature used, usually less than 5 atm. It will be appreciated that the hydrothermal treating step may be conducted in a pressure vessel.

The inventors have surprisingly found that preparing a LDH suspension in accordance with some embodiments of the first aspect of the present invention results in the formation of a stable suspension containing LDH particles in the form of dispersed platelets. The largest dimension of the particles in such stable suspensions predominantly falls within the range of 20-400 nm, more suitably 40-300 nm, with the thickness of the particles predominantly falling within the range of 5-40 nm. The particles also exhibit a narrow particle size distribution, with the particles typically showing a particle size distribution of ±20% around the average size. A reduced tendency towards aggregation has been noticed by the present inventors.

The LDH particles typically have an aspect ratio that falls within the range of from 5 to 10. In this regard, "aspect ratio" relates to the ratio of the largest dimension of the particle to its thickness or height.

The inventors have found that suspensions that include particles with a largest particle dimension of up to 400 nm, more suitably from 20 to 300 nm, form stable suspensions that do not exhibit separation or segregation.

LDH suspensions made in accordance with the method of the present invention may have up to 10% w/w LDH particles, suitably, up to 5% w/w LDH particles, even more suitably about 1% w/w LDH particles, most suitably less than 1% w/w LDH particles.

In a second aspect, the present invention provides a suspension of LDH particles in water comprising LDH particles in the form of platelets having a maximum particle dimension falling predominantly in the range of 20-400 nm, a particle concentration of up to 10% w/w, with the suspension exhibiting no settling or segregation for a period of at least one month from formation.

The particles suitably exhibit a narrow particle size distribution, with the particles typically showing a particle size distribution of ±20% around the average size of the particles. For example, if the average size of the particles is 100 nm, the particles would mostly range from 80 nm to 120 nm.

The suspension may suitably have a particle concentration of up to 10% w/w, suitably 5% w/w, more suitably about 1% w/w, even more suitably less than 1% w/w. The maximum particle dimension of the particles suitably falls in the range of 20 to 400 nm. It has been found that some suspensions containing around 10% w/w particles may exhibit a small degree of settling, possibly due to aggregation caused by "crowding" of the particles or due to insufficient dispersion of the particles.

The method of the first aspect of the present invention may further include the step of removing at least some of the water from the suspension to concentrate the particles. This may form a more concentrated suspension (i.e., one having a higher loading of particles) or even lead to the recovery of LDH particles from the suspension. The water may be removed by any suitable step known to the skilled person, such as by drying, filtration or by centrifugation followed by removal of the supernatant liquid layer. The separated LDH particles may be subsequently dried.

DETAILED DESCRIPTION OF THE PREFERRED EMBODIMENT

It will be appreciated that the drawings attached to this specification have been provided for the purposes of illustrating preferred embodiments of the present invention.

Figure 1:
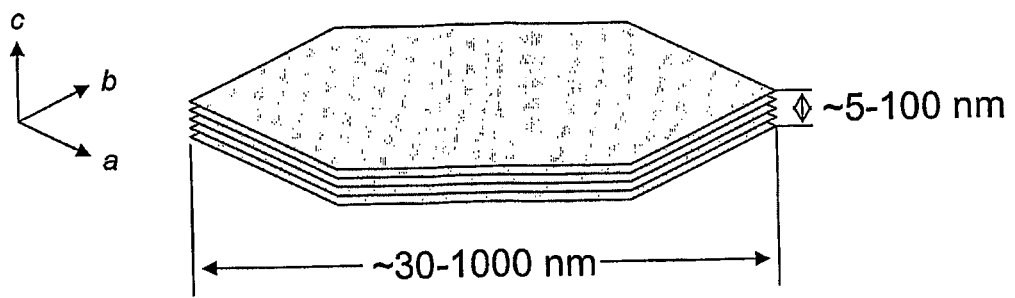
FIG. 1 shows a schematic diagram of a typical individual particle of a layered double hydroxide.

FIG. 1 shows a schematic diagram of a typical LDH particle. The typical LDH structure has metal hydroxide sheets that carry a net positive charge due to limited substitution of trivalent cations for divalent cations. As the structure includes metal hydroxide sheets, separate sheets tend to form layers one upon another, with anions or other negatively charged material being positioned between the sheets in order to balance the charge. Where anions are present between the sheets, they are often referred to interlayer anions. It has been found that interlayer anions may be exchanged or substituted.

LDH particles exhibit preferable growth along the a and b axis (as shown in FIG. 1) to form hexagonal platy sheets having an aspect ratio typically of 5-10. As can be seen from FIG. 1, the LDH particle shown schematically in FIG. 1 comprises layers 12, 14, 16, 18, 20 of hydroxide sheets. Each layer represents one positively charged brucite-like hydroxide layer (formula: $M^{II}_n M^{III}(OH)_{2(n+1)}^+$) and between two layers are anions and water molecules $(X^-.yH_2O)_z$. Although FIG. 1 shows five layers, it will be appreciated that the LDH particles may contain a greater or lesser number of brucite-like hydroxide layers. In general, there may be 5-150 such brucite-like hydroxide layers in crystalline LDH particles. Such LDH particles typically have a particle size ranging from about 30-1000 nm in the largest particle dimension, with a thickness typically from about 5-100 nm.

Figure 2:
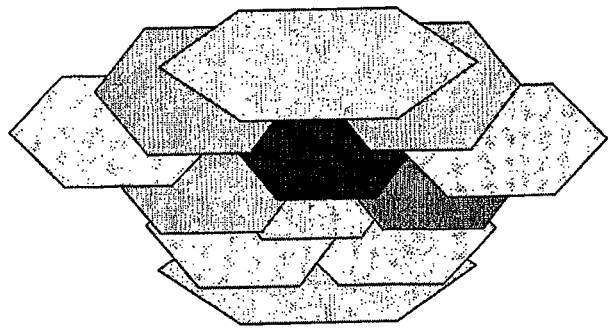
FIG. 2 shows a schematic diagram demonstrating aggregation of LDH particles.

FIG. 2 shows a schematic diagram of aggregation of individual LDH nanoparticles. It has previously been found that LDH particles tend to aggregate together when placed in suspension to form larger particles, typically having a particle size in the range of 1-10 microns. For example, the aggregated particle 22 shown schematically in FIG. 2 comprises an aggregation of a plurality of individual particles, some of which are numbered as 24, 26, 28. (Each of these individual nanoparticles is typically composed of a number of brucite-like hydroxide layers, as shown in FIG. 1.) It has been postulated that aggregation of individual LDH particles to form an aggregated particle occurs due to the following:

1) the sheets of hydroxides on the top and bottom surfaces of the individual particles are typically positively charged and also typically have anions or other negatively charged material associated therewith to balance the charge. It is possible that the surface anions or surface negatively charged material may be shared between the overlapping part of adjacent particles;
2) the individual LDH particles have some defects so that they might share some top points and edges of lattice cells; and
3) amorphus or very small particles may act as a glue between the individual platy particles.

It has been found that the aggregation of the particles causes settling of the LDH particles from suspension.

The inventors have found that the method in accordance with the first aspect of the present invention produces a suspension in which the LDH particles are dispersed and exhibit little tendency to aggregate. Accordingly, suspensions in accordance with the present invention tend to exhibit little or no segregation or settling for extended periods of time, for example, for at least one month and, in some instances, up to 6 months. Without wishing to be bound by theory, the inventors have postulated that the hydrothermal treatment step of the method of the present invention has the following effects:

a) The higher temperatures present during the hydrothermal treating step may provide extra kinetic energy for the individual LDH nanoparticles to undergo stronger Brownian motion to collide with aggregates and break aggregates into individual nanoparticles. Once these nanoparticles are separated individually, they are kept apart from one another due to the electrostatic repulsion between these nanoparticles, because these nanoparticles overall carry positive charges (zeta potential is 30-50 mV);

b) in the hydrothermal treatment step, the LDH particles become more perfect because the higher temperatures in the hydrothermal treating step allow the $M^{II}$ ions and $M^{III}$ ions in the hydroxide sheets to move around to a more desired distribution. Thus, the positive charge in each hydroxide sheet becomes more evenly distributed, thus reducing the sharing of surface anions by adjacent LDH particles;

c) some of the smaller amorphus particles probably dissolve during the hydrothermal treatment step to promote the growth of LDH crystallites.

Each of the above postulated mechanisms would act to reduce aggregation of the individual LDH particles.

The inventors have also found that there may also be benefits obtained by causing the precipitation of the LDH particles to occur very quickly. When precipitation processes take place, two processes act to form the particles, namely nucleation and growth.

In nucleation, very small particles nucleate from the solution once appropriate precipitating conditions have been reached. Nucleation of particles typically takes place on surface defects in the vessel in which precipitation is occurring or on impurities in the solution, such as dust particles in the solution. Seed particles may also be used. Further precipitation can then occur by virtue of growth, in which precipitating solids are deposited on the nucleated particles to increase the particle size of the particles, in preferred embodiments of the present invention, precipitation occurs by virtue of very rapid mixing of the mixed metal ion solution with an alkaline solution. For example, the mixed metal ion solution and an alkaline solution may be fully mixed together in less than a minute, more preferably less than 20 seconds, even more preferably less than 5 seconds, most preferably with the mixed metal ion solution and alkaline solution being mixed together in less than 2 seconds. This rapid mixing causes a high rate of nucleation of small particles.

It will also be appreciated that vigorous stirring during mixing of the mixed metal ions solution and the alkaline solution is likely to assist in preparing LDH particles having a narrow particle size distribution. It is believed that vigorous stirring may help to evenly spread the metal ions in the alkaline solution, promote the precipitation of LDH particle to occur homogeneously, and lead to a uniform LDH particle size distribution. The uniformity in LDH particles at this stage is advantageous to the stability of the suspension and uniformity of LDH particle size after the hydrothermal treatment.

It is further preferred that the mixture of precipitated particles and solution obtained from mixing the mixed metal ion solution and alkaline solution remains together for not more than 30 minutes after initial mixing. Without wishing to be bound by theory, the inventors have postulated that an aging phenomenon occurs when the precipitated particles and the solution (which is still at a slightly alkaline pH for MgAl-LDH, for example) remain together. This aging phenomenon causes redistribution of lattice ions in the hydroxide, growth of the particles and aggregation of the particles. The present inventors have further postulated that minimising the length of time of contact between the solution and the precipitated LDH particles minimises this aging phenomenon and thereby minimises growth and aggregation of the LDH particles. It is believed that this further enhances the beneficial effects of the hydrothermal treatment step.

The inventors have postulated that the rapid mixing of the salt solution and the alkaline solution within a very short time period provides an equal opportunity for each metal ion to precipitate at the same time and minimises the time for the nucleates to grow, thus resulting in relatively uniform primary LDH crystallites, which assist in obtaining monodispersed LDH particles after the hydrothermal treatment.

EXAMPLE 1

The following procedure was used to prepare a suspension in accordance with the present invention:
1) Prepare 10 mL salt solution containing 0.3 M $MgCl_2$, 0.1 M $AlCl_3$. (Solution A);
2) Prepare 40 mL 0.15 M NaOH solution (Solution B);
3) Add solution A into solution B within 2 seconds to precipitate under vigorous stirring;
4) Stir at room temperature for 10 min;
5) Separate via centrifugation;
6) Wash two times with deionized water via centrifugation;
7) Manually disperse the LDH slurry in 40 mL water and place into an autoclave;
8) Hydrothermally treat the suspension in the autoclave at 100° C. for 8 hrs;
9) Cool down the autoclave to room temperature and store the suspension.

This suspension contained about 0.4% w/w $Mg_2Al(OH)_6Cl.H_2O$, with the product yield being about 60%.

Figure 3:
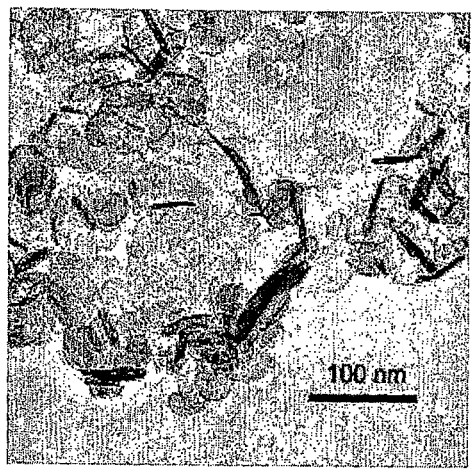
FIG. 3 shows TEM images of LDH particles from a suspension in accordance with an embodiment of the present invention and from an ethanol suspension of LDH prepared by a conventional method.
Figure 3:
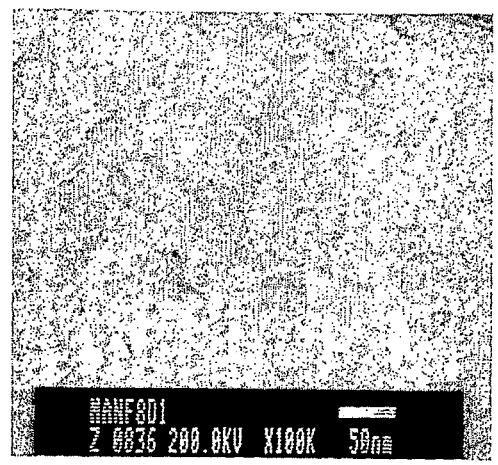

FIG. 3 shows a photomicrograph of a suspension made in accordance with the above procedure, which shows well dispersed, hexagonal shaped particles. FIG. 3 also shows a photomicrograph of an LDH suspension prepared by a conventional method and then dispersed in ethanol. This shows much less well dispersed particles that still exhibit apparent aggregation.

EXAMPLE 2

The following procedure was used to prepare a suspension in accordance with the present invention:
1) Prepare 10 mL salt solution containing 0.2 M $Co(NO_3)_2$, 0.1 M $Al(NO_3)_3$. (Solution A);
2) Prepare 40 mL alkaline solution 0.15 M NaOH and 0.013 M $Na_2CO_3$ (Solution B);
3) Add solution A into solution B within 2 seconds to precipitate under vigorous stirring;
4) Stir at room temperature for 30 min;
5) Separate via centrifugation (pH≈10);
6) Wash two times with deionzed water via centrifugation;
7) Manually disperse the LDH slurry in 40 mL water and place into an autoclave;
8) Hydrothermally treat the suspension in the autoclave at 100° C. for 8 hrs;
9) Cool down the autoclave to room temperature and store the suspension. This suspension contains about 0.5% w/w $Co_2Al(OH)_6(CO_3)_{0.5}.H_2O$, the product yield is about 60%.

EXAMPLE 3

The following procedure was used to prepare a suspension in accordance with the present invention:
1) Prepare 10 mL salt solution containing 0.3 M $Mg(NO_3)_2$ and 0.1 M $Al(NO_3)_3$ (Solution A);
2) Prepare 40 mL 0.15 M NaOH (Solution B);
3) Add 10 mL solution A into 40 mL solution B to precipitate under vigorous stirring;
4) Stir at room temperature for 10 min;
5) Separate via centrifugation;
6) Wash two times with deionized water via centrifugation;
7) Disperse the slurry in 40 mL water and place into an autoclave (45 mL);

8) Heat the autoclave at 100° C. for 16 hrs.
9) Cool down the autoclave to room temperature and store the suspension. This suspension contains about 0.4% w/w $Mg_2Al(OH)_6NO_3 \cdot H_2O$, the product yield is about 60%.

EXAMPLE 4

The following procedure was used to prepare a suspension in accordance with the present invention:
1) Prepare 10 mL salt solution containing 0.3 M $MgCl_2$ and 0.1 M $AlCl_3$ (Solution A);
2) Prepare 40 mL 0.15 M NaOH and 0.013 M $Na_2CO_3$ (Solution B);
3) Add 10 mL solution A into 40 mL solution B to precipitate under vigorous stirring;
4) Stir at room temperature for 10 min;
5) Separate via centrifugation;
6) Wash two times with deionized water via centrifugation;
7) Disperse the slurry in 40 mL water and place into an autoclave (45 mL);
8) Heat the autoclave at 100° C. for 16 hrs.
9) Cool down the autoclave to room temperature and store the suspension.
This suspension contains about 0.45% w/w $Mg_3Al(OH)_8(CO_3)_{0.5} \cdot H_2O$, the product yield is about 60%.

EXAMPLE 5

The following procedure was used to prepare a suspension in accordance with the present invention:
1) Prepare 10 mL salt solution containing 0.3 M $MgCl_2$, 0.04 M $FeCl_3$ and 0.06 M $AlCl_3$ (Solution A);
2) Prepare 40 mL 0.15 M NaOH (Solution B);
3) Add 10 mL solution A into 40 mL solution B to precipitate under vigorous stirring;
4) Stir at room temperature for 10 min;
5) Separate via centrifugation;
6) Wash two times with deionized water via centrifugation;
7) Disperse the slurry in 40 mL water and place into an autoclave (45 mL);
8) Heat the autoclave at 100° C. for 16 hrs.
9) Cool down the autoclave to room temperature and store the suspension.
This suspension contains about 0.4% w/w $_{Mg2}Fe_{0.04}Al_{0.06}(OH)_2Cl \cdot H_2O$, the product yield is about 60%.

EXAMPLE 6

The following procedure was used to prepare a suspension in accordance with the present invention:
1) Prepare 10 mL salt solution containing 0.3 M $MgCl_2$ and 0.1 M $AlCl_3$ (Solution A);
2) Prepare 40 mL 0.15 M NaOH (Solution B);
3) Add 10 mL solution A into 40 mL solution B to precipitate under vigorous stirring;
4) Stir at room temperature for 10 min;
5) Separate via centrifugation;
6) LDH slurry is exchanged with $Na_2SO_4$ (40 mL 0.05 M) for 30 min;
7) Separation and then wash 1 time;
8) Disperse the slurry in 40 mL water and place into an autoclave (45 mL);
9) Heat the autoclave at 100° C. for 16 hrs.
10) Cool down the autoclave to room temperature and store the suspension.
This suspension contains about 0.4% w/w $Mg_2Al(OH)_6(SO_4)_{0.5} \cdot H_2O$, the product yield is about 60%.

Figure 4:
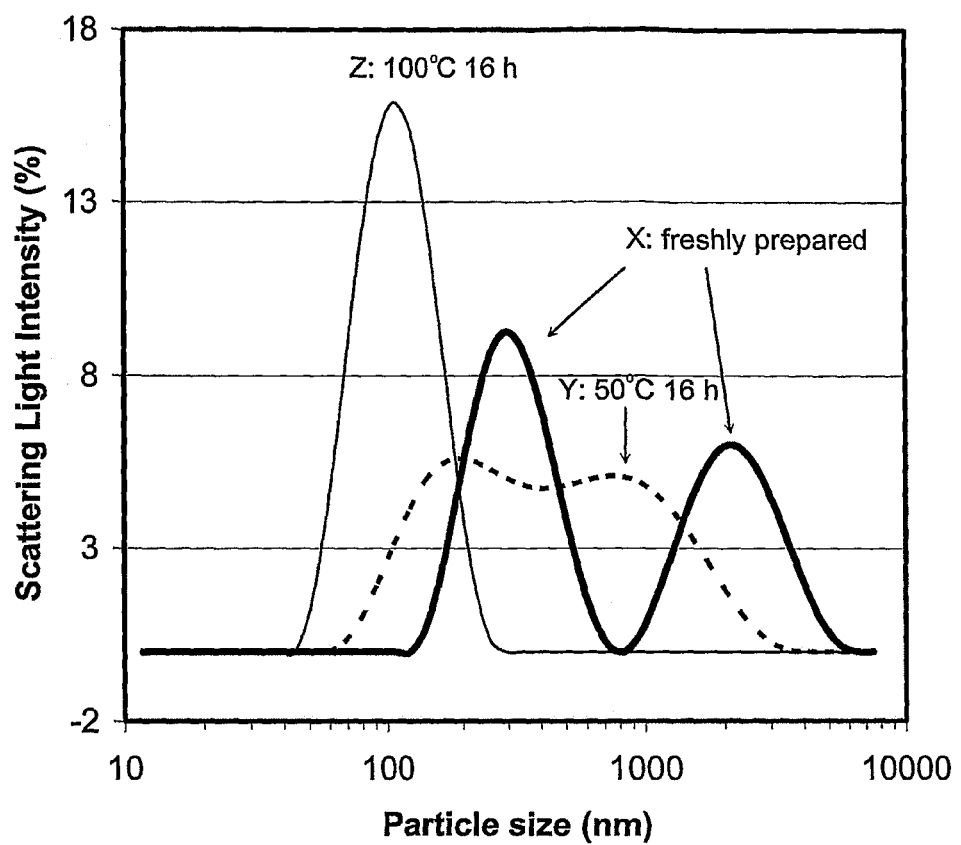
FIG. 4 shows the particle size distribution of $Mg_2Al$—Cl-LDH samples: (X) stirred for 10 minutes at room temperature, and then dispersed with ultrasonic treatment for 20 minutes, with two peaks at 320 nm and 2300 nm; (Y) aged at 50° C. for 18 hours, and dispersed with ultrasonic treatment for 20 minutes, with two broad peaks at 220 nm and 955 nm; (Z) as-prepared with the current method, with one sharp peak at 114 nm.

FIG. 4 shows a graphical representation of the particle size distribution of suspensions of LDH particles prepared in accordance with the present invention (line Z in FIG. 4), the particle size distribution of freshly prepared LDH precipitates that have been subjected to ultrasonication for 20 minutes (i.e. no hydrothermal treatment, Line X in FIG. 4) and the particle size distribution of fresh LDH precipitates that have been subjected to ultrasonication for 20 minutes and aged overnight at 50° C. (line Y in FIG. 4). The particle size distribution was measured using photon correlation spectroscopy (PCS).

The $Mg_2Al$—Cl-LDH suspension obtained after hydrothermal treatment at 100° C. for 16 hours has a narrow particle size distribution with an equivalent hydrodynamic diameter of 114 run, with all particles inclusively within 45-250 nm. However, the suspensions of the same LDH material made conventionally without a hydrothermal treatment and dispersed with the assistance of ultrasonication in water have a much wider particle size distribution and larger diameters (200-3000 nm). In particular, the suspension of freshly precipitated $Mg_2Al$—Cl-LDH, after ultrasonication for 20 min, consists of a bimodal particle size distribution, with diameters at 320 nm and 2300 nm, respectively. After aging at 50° C. overnight, the aggregates decrease in size to 220-955 nm. This means that the aggregates can be only partially segregated after aging and/or ultrasonication. However, the inventor's experiments have demonstrated that these partially segregated particles can be also segregated further into individual nanoparticles by the process of the present invention. Visually, the well-dispersed suspension looks very transparent while the conventional ones are turbid. These evidences suggest that the aggregates are completely segregated and well dispersed into much smaller particles after the hydrothermal treatment at 100° C. for 16 hours.

Figure 5:
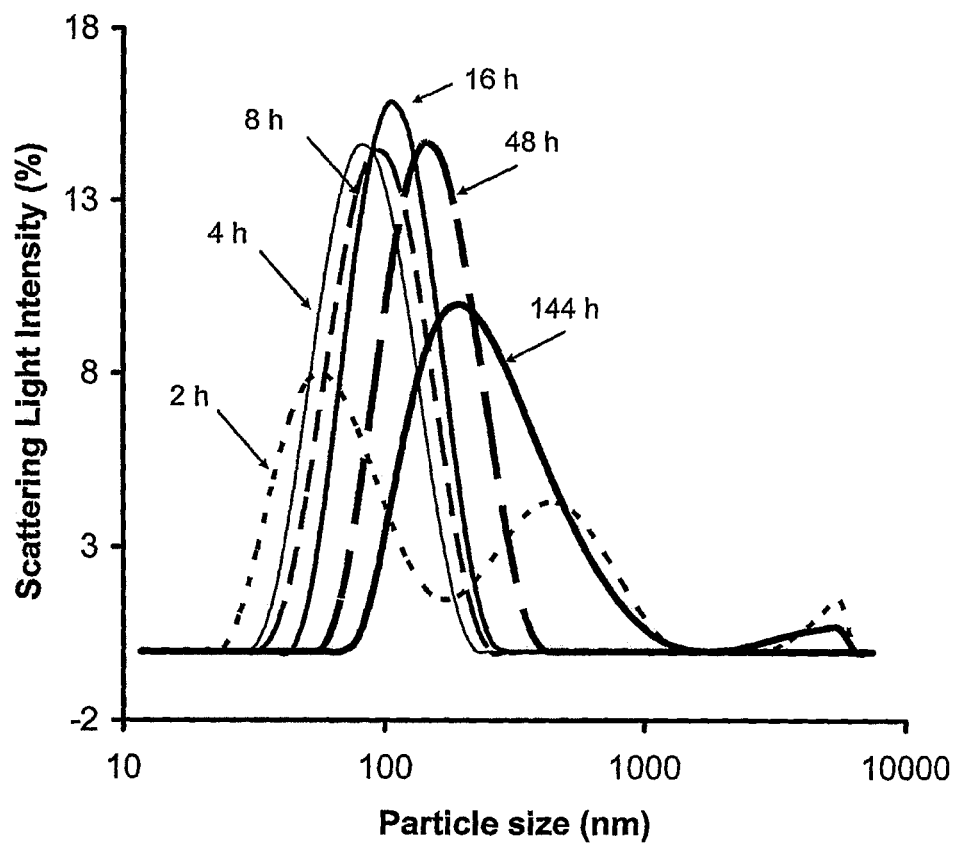
FIG. 5 shows the dispersion of $Mg_2Al$—Cl-LDH aggregates with heating duration during the hydrothermal treatment at 100° C.

FIG. 5 shows a graphical representation of particle size distribution for LDH suspensions subjected to hydrothermal treatments of differing duration and a hydrothermal treatment temperature of 100° C. As can be seen from FIG. 5, after hydrothermal treatment at 100° C. for a suitable period of time (4, 8, 16 or 48 hours), the LDH particles in as-made $Mg_2Al$—Cl-LDH suspensions become very uniform, with a narrow particle size distribution. However, the 2-hour or 144-hour treatment leads to extra distribution bands with much bigger particles (FIG. 5), indicating the presence of some degree of aggregation. It seems that 2-hour heat treatment at 100° C. does not disperse all aggregates into individual LDH crystallites. Compared with the freshly prepared LDH suspension (FIG. 4, curve X), 2-hour treated LDH suspension contains much smaller particles (69 vs. 320 nm), which further suggests that the freshly prepared LDH aggregates are only partially segregated with ultrasonication. However, there are two groups of bigger particles with size of 800 nm and over 4 μm, respectively. Subsequently, these two groups of particles disappeared when the treatment time is extended to 4 hours, resulting in one narrow particle size distribution band (89 nm) in the LDH suspension. This suggests that 2-hour treatment at 100° C. is not sufficient to fully disperse the aggregates while the 4-hour treatment completes the segregation of LDH particles. As the treatment time increases further, the LDH particle size distribution band is shifted to the big particle size side, indicating the continuous growth of LDH particles with time. However, if the hydrothermal treatment is continued to 144 hours at 100° C., the LDH particle size distribution band becomes quite broad and the LDH crystallite size is hundreds of nanometers. As a consequence, a weak and broad band is seen around 5 μm, presumably due to the re-aggregation of these bigger LDH crystallites.

The above results suggest that, for the shorter hydrothermal treatment times in the present invention, temperatures in the upper part of the treatment temperature range should be used, whilst at the longer hydrothermal treatment times, temperatures in the lower part of the range should be used.

Figure 6:
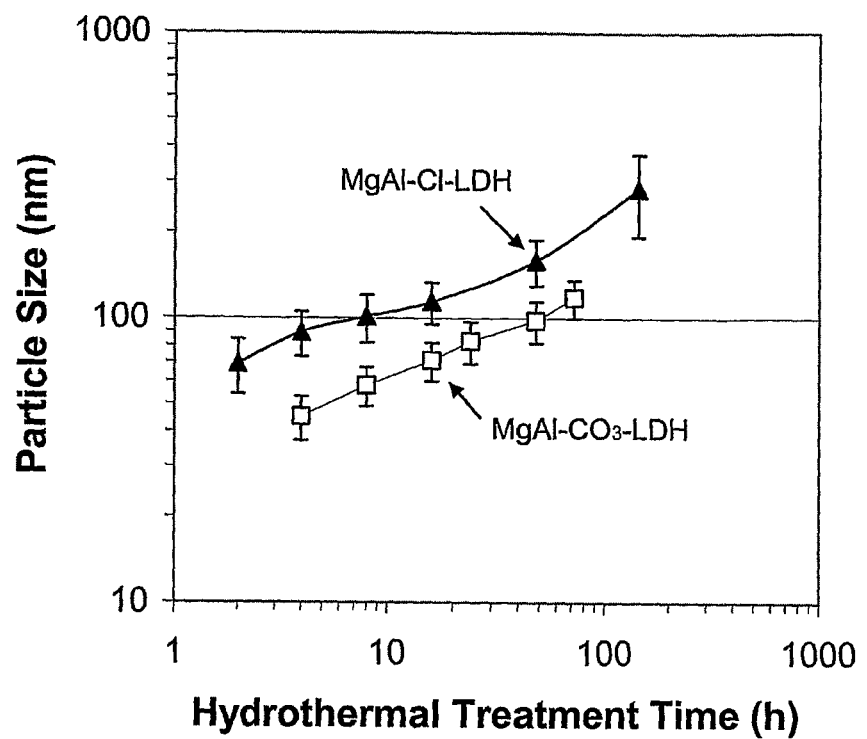
FIG. 6 shows the relationship between primary particle size of the LDH particles and duration of the hydrothermal treatment step, for hydrothermal treatment steps utilizing a temperature of 100° C.

Regardless of the aggregates, the primary $Mg_2Al$—Cl-LDH particle size, i.e. the peak value from PCS curves in FIG. 5 constantly increase from 70 to 300 nm with increasing the hydrothermal treatment time from 2 to 144 hours, as clearly shown in FIG. 6 (bold curve). The relationship is almost linear, indicating a rough growth rate of 1.5 nm per hour. It is therefore concluded that the $Mg_2Al$—Cl-LDH particle size can be tailored in the range of 70-300 nm by adjusting hydrothermal treatment time at 100° C.

In the case of $Mg_2Al$—$CO_3$-LDHs (i.e. $CO_3$ being the interlayer anion), the relationship between the treatment time and the LDH particle size is quite similar. As shown in FIG. 6 (thin curve), the hydrodynamic diameter of LDH-$CO_3$ particles almost linearly increase from 45 to 118 nm with the time from 4 to 72 hours in the logarithmic scale. Very interestingly, the average particle size of LDH-$CO_3$ is smaller roughly by 40-50 nm than that of LDH-Cl at every identical time point, suggesting a similar growth pattern but different growth preference in these two systems.

The effect of hydrothermal treatment temperature was also investigated. Table 1 shows the particle size of $Mg_2Al$—Cl-LDH under the various hydrothermal treatments as specified in Table 1.

TABLE 1

$Mg_2Al$-LDH-Cl particle size (nm) under different conditions.

| time | 80° C. | 100° C. | 125° C. | 150° C. |
|---|---|---|---|---|
| 2 hr | | 69 ± 15 | 89 ± 19 | 94 ± 20 |
| | | (465 ± 110) | | |
| 4 hr | 99 ± 36[a] | 89 ± 16 | 111 ± 22 | 118 ± 18 |
| | (2500 ± 660)[b] | | | (3300 ± 540) |
| 8 hr | 87 ± 19 | 101 ± 19 | 124 ± 30 | 160 ± 30 |
| | | | | (4600 ± 420) |
| 16 hr | 92 ± 18 | 114 ± 19 | 162 ± 46 | 194 ± 34 |
| | | | (4200 ± 500) | (4300 ± 520) |
| 48 hr | | 159 ± 29 | | |
| 144 hr | | 284 ± 91 | | |
| | | (4200 ± 500) | | |

Note:
[a] The peak value and the peak width at half maximum of small particles are from the particle size distribution on intensity average.
[b] The data in the parenthesis are corresponding to big size particles that are not dispersed or re-aggregated.

The treatment temperature seems to more strongly influence LDH particle size than treatment time. As given in Table 1 for $Mg_2Al$—Cl-LDHs, an increase in temperature by 10° C. can lead to an increase in the hydrodynamic diameter by 10-15 nm on average after hydrothermal treatment for 8 or 16 hours, or the primary particle size is doubled when temperature increases from 80 to 150° C. for treatment time of 8 or 16 hours. This shows the quick growth of LDH crystallites at higher temperatures. In contrast, if treatment time is short, such as 2 or 4 hours, the particle growth seems to be much slower (3-5 nm per 10° C.). This comparison suggests that in the beginning of hydrothermal treatment, the major event is segregation of LDH aggregates to individual LDH crystallites in the aqueous suspension. Subsequently LDH crystallites grow continuously with time.

Similarly, incomplete dispersion is observed at lower temperatures for short treatment duration while re-aggregation takes place at higher temperatures even at short treatment time (see Table 1). For example, the treatment at 80° C. for 4 hours does not disperse all the aggregates while the treatment at 150° C. for 4 hours is long enough to produce bigger LDH crystallites to re-form the micrometer-scaled aggregates.

A number of LDH suspensions were prepared in accordance with the present invention. Table 2 summarises the conditions under which the suspensions were prepared and gives the average particle size and the measured zeta potentials.

TABLE 2

Summary of Mg2Al-LDH Particle size and Zeta potential

| Compounds[a] | Conditions | Particle size (nm) | ξ Potential (mV) |
|---|---|---|---|
| $Mg_2Al$—Cl-LDH | 100° C., 4 h, 0.4%[b] | 89, 95, 97, 87, 92[c] | 51.9 |
| | 100° C., 8 h, 0.4% | 101 | 48.3 |
| | 100° C., 16 h, 0.4% | 114 | 47.0 |
| | 100° C., 48 h, 0.4% | 159, 159, 171, 160 | 49.1 |
| | 100° C., 144 h, 0.4% | 284 | 47.9 |
| | 100° C., 16 h, 1.0% | 101 | 53.0 |
| | 100° C., 16 h, 2.0% | 116 | 51.3 |
| | 100° C., 16 h, 3.0% | 115 | 45.0 |
| | 100° C., 16 h, 4.0% | 120 | 50.4 |
| | 100° C., 72 h, 1.0% | 155 | — |
| | 80° C., 8 h, 1.0% | 85 | 38.5 |
| | 80° C., 16 h, 1.0% | 89 | 36.9 |
| $Mg_2Al$—$CO_3$-LDH | 100° C., 4 h, 0.4% | 46, 43 | 39.5, 48.5 |
| | 100° C., 8 h, 0.4% | 58 | 37.2 |
| | 100° C., 16 h, 0.4% | 75, 71, 68 | 42.0, 48.9 |
| | 100° C., 72 h, 0.4% | 118 | 48.5 |

TABLE 2-continued

Summary of Mg2Al-LDH Particle size and Zeta potential

| Compounds[a] | Conditions | Particle size (nm) | ξ Potential (mV) |
|---|---|---|---|
| $Mg_2Al$—$NO_3$-LDH | 100° C., 16 h, 0.4% | 112, 117, 119 | — |
| $Mg_2Al$—$SO_4$-LDH | 100° C., 16 h, 0.4% | 142 | 28.4, 28.1 |
| $Mg_3Al$—Cl-LDH | 100° C., 16 h, 0.4% | 106 | 43.8, 45.7 |
| $Mg_3Al$—$CO_3$-LDH | 100° C., 16 h, 0.4% | 143 | 33.6 |
| $Ni_2Al$—$CO_3$-LDH | 100° C., 16 h, 0.5% | 41, 43 | 40.6, 41.2 |
| $Co_2Al$—Cl-LDH | 100° C., 16 h, 0.25% | 127 | 37.2, 38.1 |
| $Co_{0.5}Mg_{1.5}Al$—Cl-LDH | 100° C., 16 h, 0.2% | 125 | 43.1, 42.8 |
| $Mg_2Al_{0.7}Fe^{III}{}_{0.3}$—Cl-LDH | 100° C., 16 h, 0.4% | 123 | — |
| $Mg_2Al_{0.6}Fe^{III}{}_{0.4}$—Cl-LDH | 100° C., 16 h, 0.4% | 110 | 37.7, 39.0 |
| $Mg_2Al_{0.5}Fe^{III}{}_{0.5}$—Cl-LDH | 100° C., 16 h, 0.4% | 90 | — |

Note:
[a]The composition of compound is nominal.
[b]This indicates that the suspension was hydrothermally treated at 100° C. for 4 hours, with nominal LDH weight percentage of 0.4% in the suspension.
[c]Multiple value was obtained from different repeated suspensions.

The present invention provides a suspension of LDH particles in water and a method for preparing such a suspension. In some embodiments, the suspension is stable for extended periods of time and will typically not exhibit any separation or segregation for up to a month from formation. Suitably, such stable suspensions will not exhibit separation or segregation for a period of up to 6 months from formation. The suspension includes LDH particles having a narrow particle size distribution, with the largest particle dimension of the particles predominantly falling within the range of 20-400 nm, more suitably 40-300 nm. The suspension may contain up to 10% w/w LDH particles, although the suspensions more preferably contain 1% w/w or less LDH particles. Unlike Liu et al, which shakes and heats the suspension at atmospheric pressure, the present invention utilises a hydrothermal heating step. The present invention also uses higher heating temperatures and, in some embodiments, different conditions in the co-precipitation step, when compared to Liu et al. In particular, Liu et al is specific in directing the reader to age the precipitated particles and alkaline solution formed in the precipitation step for 1 hour. In contrast, the present inventors have found that the precipitated particles and the solution remaining after precipitation should desirably remain in contact with each other for not longer than 30 minutes.

The suspensions in accordance with the present invention may be used in biomedical applications, for example, to prepare bio-inorganic hybrid composites as described in European patent application no. 987328, the entire contents of which are herein incorporated by cross reference. The suspension may be also used to manufacture polymer/clay nanocomposites for membrane separation, biomedical materials and other uses. The suspensions may also be useful as a component in the manufacture of polymers, with the LDH nanoparticles acting as a filler in the polymer.

The current invention can be used to make, for example LDH where the interlayer anion is chloride, nitrate, sulfate, and carbonate. Where the suspension is to be used in an application that requires exchange of the interlayer anion, LDH-carbonate is not preferred, but it is a good candidate to make polymer-LDH nanocomposite as well as polymer fillers, retardants etc. In some cases, $LDH$-$CO_3$ can be exchanged with $Cl^-$, $NO_3^-$ and $SO_4^{2-}$ in a lightly acidic solution.

If it is desired to make LDH that is free of carbonate as the interlayer anion, it is preferred to conduct the co-precipitation step in an inert atmosphere, such as in a nitrogen atmosphere, because air contains carbon dioxide that may be absorbed by the solutions, leading to carbonate ions going into the interlayer space, or in a carbon dioxide or carbonate free environment.

Those skilled in the art will appreciate that the present invention may be susceptible to variations and modifications other than those specifically described. It is to be understood that the present invention encompasses all such variations and modifications that fall within its spirit and scope.

What is claimed is:

1. A method for preparing a suspension of layered double hydroxide (LDH) particles comprising the steps of:
   a) preparing LDH precipitates by coprecipitation to form a mixture of LDH precipitates and solution;
   b) separating the LDH precipitates from the solution;
   c) washing the LDH precipitates to remove residual ions;
   d) mixing the LDH precipitates with water; and
   e) subjecting the mixture of LDH precipitates and water from step (d) to a hydrothermal treatment step by heating to a temperature of from greater than 80° C. to 150° C. for a period of about 2 hour to about 48 hours to form a well dispersed suspension of LDH particles in water, wherein said LDH particles have a maximum particle dimension of up to 400 nm, made such that said LDH particles are well-dispersed in a stable suspension and exhibit a particle size distribution of no more than ±24%, based upon the peak value and the peak width at half maximum from the particle size distribution of an intensity average using photon correlation spectroscopy (PCS) measurement.

2. A method as claimed in claim 1 wherein the LDH precipitates and the solution formed in step (a) are left in contact with each other for a period not exceeding 30 minutes.

3. A method as claimed in claim 1 wherein the LDH precipitates and the solution formed in step (a) are left in contact with each other for a period not exceeding 20 minutes.

4. A method as claimed in claim 1 wherein the LDH precipitates and the solution formed in step (a) are left in contact with each other for a period not exceeding 10 minutes.

5. A method as claimed in claim 1 wherein the LDH precipitates and the solution formed in step (a) are left in contact with each other for a period not exceeding 5 minutes.

6. A method as claimed in claim 1 wherein the LDH precipitates and the solution formed in step (a) are left in contact with each other for a period not exceeding 1 minute.

7. A method as claimed in claim 1 wherein the LDH precipitates and solution formed in step (a) are stirred or agitated.

8. A method as claimed in claim 1 wherein the hydrothermal treating step is carried out whilst suppressing boiling.

9. A method as claimed in claim 1 wherein in step (a) a mixed metal ion solution and an alkaline solution are rapidly mixed together.

10. A method as claimed in claim 9 wherein the mixed metal ion solution and the alkaline solution are added together within a time period of less than 1 minute.

11. A method as claimed in claim 1 wherein precipitation in step (a) takes place at a temperature ranging from room temperature up to about 50° C.

12. A method as claimed in claim 1 wherein the LDH precipitates are washed one or more times with deionized water following separation from the solution.

13. A method as claimed in claim 1 wherein the temperature in the hydrothermal treating step is within the range of from greater than 80° C. to 120° C.

14. A method as claimed in claim 1 wherein the mixture of water and LDH precipitates is held at the elevated temperature for a period of from 4-48 hours.

15. A method as claimed in claim 14 wherein the mixture of water and LDH precipitates is held at the elevated temperature for a period of from 4-24 hours.

16. A method as claimed in claim 1 wherein the largest dimension of the particles in the suspension predominantly falls within the range of 20-400 nm, with the thickness of the particles predominantly falling within the range of 5-40 nm and wherein the particles show a particle size distribution of ±20% around the average size.

17. A method as claimed in claim 1 wherein the largest dimension of the particles in the suspension predominantly falls within the range of 40-300 nm.

18. A method as claimed in claim 1 wherein the suspension contains up to 10% w/w LDH particles.

19. A method as claimed in claim 1 wherein the suspension contains up to 5% w/w LDH particles.

20. A method as claimed in claim 1 wherein the suspension contains up to about 1% w/w LDH particles.

21. A method as claimed in claim 1 wherein the suspension contains less than 1% w/w LDH particles.

22. A method as claimed in claim 1 further comprising the step of removing at least some of the water from the suspension to concentrate the particles to form a more concentrated suspension.

23. A method for forming LDH particles comprising forming a suspension as claimed in claim 1 and separating the LDH particles from the suspension.

24. A method as claimed in claim 1 wherein step (e) comprises subjecting the mixture of LDH precipitates and water from step (d) to a hydrothermal treatment step by heating to a temperature of from greater than 80° C. to 150° C. for a period of about 4 hours to about 48 hours to form a well dispersed suspension of LDH particles in water, wherein said LDH particles have a maximum particle dimension of from 20 nm to 400 nm, made such that said LDH particles are well dispersed in a stable suspension and said LDH particles exhibit a particle size distribution of no more than ±20%, based upon the peak value and the peak width at half maximum from the particle size distribution of an intensity average using PCS measurement.

* * * * *